United States Patent
Xu et al.

(10) Patent No.: US 8,064,732 B2
(45) Date of Patent: Nov. 22, 2011

(54) FIELD OF VIEW CALIBRATION FOR MODULAR NUCLEAR MEDICAL IMAGING SYSTEM

(75) Inventors: Ray S. Xu, Algonquin, IL (US); James T. Chapman, Glen Ellyn, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 685 days.

(21) Appl. No.: 12/240,790

(22) Filed: Sep. 29, 2008

(65) Prior Publication Data
US 2009/0086925 A1    Apr. 2, 2009

Related U.S. Application Data

(60) Provisional application No. 60/995,578, filed on Sep. 27, 2007, provisional application No. 60/995,576, filed on Sep. 27, 2007, provisional application No. 60/995,528, filed on Sep. 27, 2007.

(51) Int. Cl.
G06K 9/32    (2006.01)

(52) U.S. Cl. ... 382/294; 382/295; 382/296; 250/363.04; 250/363.01; 324/307; 324/322

(58) Field of Classification Search .............. 382/294, 382/295, 296; 250/363.04, 363.01; 324/307, 324/322
See application file for complete search history.

(56) References Cited

U.S. PATENT DOCUMENTS

2006/0058641 A1* 3/2006 Krieg et al. .......... 600/416
2008/0073543 A1* 3/2008 Vija et al. ........... 250/370.08

* cited by examiner

*Primary Examiner* — Mike Rahmjoo
(74) *Attorney, Agent, or Firm* — Peter L. Kendall

(57) ABSTRACT

A method and apparatus for correcting misalignment between fields of view of a CT device and a NM device of a modular multimodality medical imaging system, by providing a Field Of View Calibration Matrix (FOV-CM) containing rotational and translational transformations between coordinate systems of the CT and NM systems.

8 Claims, 3 Drawing Sheets

FIELD OF VIEW CALIBRATION FOR MODULAR NUCLEAR MEDICAL IMAGING SYSTEM

CROSS-REFERENCES TO RELATED APPLICATIONS

This application claims benefit under 35 U.S.C. §119(e) to:
U.S. Provisional Patent Application Ser. No. 60/995,528 filed on Sep. 27, 2007;
U.S. Provisional Patent Application Ser. No. 60/995,576 filed on Sep. 27, 2007; and
U.S. Provisional Patent Application Ser. No. 60/995,578 filed on Sep. 27, 2007,
which are hereby incorporated by reference in their entireties.

BACKGROUND OF THE INVENTION

The present invention relates to correcting misalignment between Computed Tomography (CT) and Nuclear Medical (NM) images in modular Nuclear Medical imaging Systems.

For loosely-coupled modular multi-modality imaging systems, such as cardiac SPECT-CT systems that share the same patient table, but do not have any common installation platform, it is necessary to calibrate the separate imaging modules so that their images may be fused or combined into a composite image that is clinically useful.

BRIEF SUMMARY OF THE INVENTION

The present invention provides a method and apparatus for correcting misalignment between fields of view of a CT device and a NM device of a modular multimodality medical imaging system, by providing a Field Of View Calibration Matrix (FOV-CM) containing rotational and translational transformations between coordinate systems of the CT and NM systems.

BRIEF DESCRIPTION OF THE DRAWINGS

These and other features, aspects, and advantages of the present invention will become better understood with reference to the following description and appended claims, and accompanying drawings where:

Figure 1:
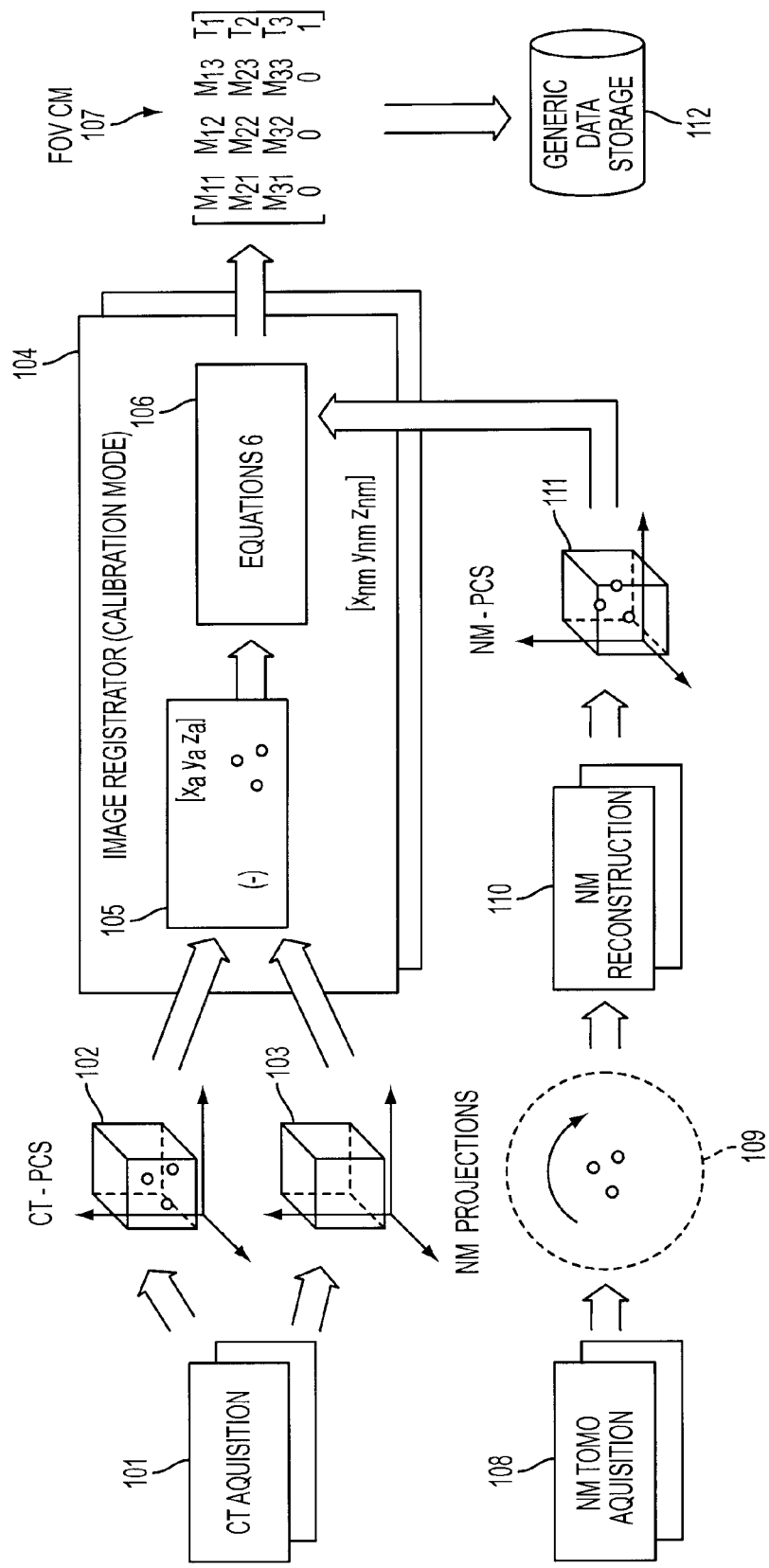
FIG. 1: shows a function block diagram representing how to generate a field of view (FOV) calibration matrix (CM)

The figures illustrate diagrams of the functional blocks of various embodiments. The functional blocks are not necessarily indicative of any division between hardware circuitry. Thus, for example, one or more of the functional blocks (e.g., processors or memories) may be implemented in a single piece of hardware (e.g., a general purpose signal processor or a block or random access memory, hard disk or the like). Similarly, the programs may be stand alone programs, may be incorporated as subroutines in an operating system, may be functions in an installed imaging software package, and the like.

It should be understood that the various embodiments are not limited to the arrangements and instrumentality shown in the drawings.

DETAILED DESCRIPTION OF THE INVENTION

The present invention may be understood more readily by reference to the following detailed description of preferred embodiments of the invention as well as to the examples included therein.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

According to one embodiment of the present invention a Field of View Calibration Matrix (FOV-CM) is defined mathematically. A 4×4 FOV-CM representing a rigid orthogonal transformation of a spatial position from one coordinate system to another (here, a NM coordinate system and a CT coordinate system), according to preferred embodiments of the present invention, is shown below:

$$\begin{bmatrix} M_{11} & M_{12} & M_{13} & T_1 \\ M_{21} & M_{22} & M_{23} & T_2 \\ M_{31} & M_{32} & M_{33} & T_3 \\ 0 & 0 & 0 & 1 \end{bmatrix}. \qquad 1$$

where the M values represent rotational transformations between the various axes of the coordinate systems and the T values represent translational transformations between origins of the coordinate systems.

Thus, the respective rotational and translational transformations in the 4×4 FOV-CM shown above are represented by the following submatrices:

$$\begin{bmatrix} M_{11} & M_{12} & M_{13} \\ M_{21} & M_{22} & M_{23} \\ M_{31} & M_{32} & M_{33} \end{bmatrix} \text{ and } \begin{bmatrix} T_1 \\ T_2 \\ T_3 \end{bmatrix}. \qquad 2$$

The transformation of the coordinates of a spatial point in the "unprimed" system [x, y, z] to the "primed" system [x', y', z'] is preferably represented as follows:

$$\begin{bmatrix} x' \\ y' \\ z' \\ 1 \end{bmatrix} = \begin{bmatrix} M_{11} & M_{12} & M_{13} & T_1 \\ M_{21} & M_{22} & M_{23} & T_2 \\ M_{31} & M_{32} & M_{33} & T_3 \\ 0 & 0 & 0 & 1 \end{bmatrix} \begin{bmatrix} x \\ y \\ z \\ 1 \end{bmatrix}. \qquad 3$$

The $1^{st}$ column $[M_{11}, M_{21}, M_{31}]$ contains the directional cosines of the X-axis with respect to X', Y', and Z' axes.

The $2^{nd}$ column $[M_{12}, M_{22}, M_{32}]$ contains the directional cosines of the Y-axis with respect to X', Y', and Z' axes.

The $3^{rd}$ column $[M_{13}, M_{23}, M_{33}]$ contains the directional cosines of the Z-axis with respect to X', Y', and Z' axes.

The $4^{th}$ column $[T_1, T_2, T_3]$ is the coordinates of the origin, i.e., [0, 0, 0], in the "primed" system.

In the modular NM imaging system according to various embodiments of the present invention, both CT transverse images and NM volumes are preferably reconstructed in the DICOM patient coordinate system (PCS). The PCS system is defined consistently in reference to both CT device coordinate system (DCS) and NM DCS. CT and NM volumes are preferably co-registered based on the same mechanical references, as described in U.S. Provisional Patent Application Ser. No. 60/995,528 filed on Sep. 27, 2007, which is hereby incorporated by reference in its entirety.

Due to mechanical and installation errors, the two patient coordinate systems used in CT and NM reconstructions do not always align with each other. The FOV-CM is designed to capture the difference. Particularly preferably, the FOV-CM captures the difference of the NM PCS with respect to the CT PCS:

$$\begin{bmatrix} x_{ct} \\ y_{ct} \\ z_{ct} \\ 1 \end{bmatrix} = \begin{bmatrix} M_{11} & M_{12} & M_{13} & T_1 \\ M_{21} & M_{22} & M_{23} & T_2 \\ M_{31} & M_{32} & M_{33} & T_3 \\ 0 & 0 & 0 & 1 \end{bmatrix} \begin{bmatrix} x_{nm} \\ y_{nm} \\ z_{nm} \\ 1 \end{bmatrix}. \qquad 4$$

For a perfectly aligned CT-NM system, the FOV-CM preferably becomes a unit matrix, as shown below:

$$\begin{bmatrix} x_{ct} \\ y_{ct} \\ z_{ct} \\ 1 \end{bmatrix} = \begin{bmatrix} 1 & 0 & 0 & 0 \\ 0 & 1 & 0 & 0 \\ 0 & 0 & 1 & 0 \\ 0 & 0 & 0 & 1 \end{bmatrix} \begin{bmatrix} x_{nm} \\ y_{nm} \\ z_{nm} \\ 1 \end{bmatrix}. \qquad 5$$

The $3^{rd}$ column of FOV-CM, as shown in Matrix 1, is preferably not independent. The directional cosines of the Z-axis are preferably derived after the directional cosines of the other two axes are determined. Therefore, there are preferably only 9 independent variables in a FOV-CM and at a minimum 9 uncorrelated equations are needed to derive a FOV-CM. Since a spatial point provides measurements that satisfy the following three equations:

$$x_{ct} = x_{nm}*M_{11} + y_{nm}*M_{12} + z_{nm}*M_{13} + T_1$$

$$y_{ct} = x_{nm}*M_{21} + y_{nm}*M_{22} + z_{nm}*M_{23} + T_2$$

$$z_{ct} = x_{nm}*M_{31} + y_{nm}*M_{32} + z_{nm}*M_{33} + T_3 \qquad 6,$$

only three point positions need to be measured to determine the FOV-CM for the modular Nuclear Medicine imaging system according to the present invention. The three points preferably do not lie along the same line to ensure the independence among the equations.

With no redundant measurement, however, errors in those measured points will be accumulated linearly to the calculated field of view calibration matrix (FOV-CM). It is preferable to measure more than three points to achieve error reduction via statistical redundancy.

Various embodiments of the present invention preferably provide a field of view (FOV) calibration. The FOV calibration is preferably a procedure to create a field of view calibration matrix (FOV-CM) associated with an installed modular Nuclear Medical imaging system. The FOV calibration, according to the present invention is preferably performed after the system is installed.

As shown in FIG. 1, the NM Tomo Acquisition (108) preferably acquires the projections (109) of a set of hot point sources. The projections are preferably reconstructed (110) and the PCS coordinates (111) are set into the reconstructed NM image based on the co-registration scheme as described in the above-mentioned provisional application Ser. No. 60/995,528. The CT Acquisition (101) preferably acquires two contrast enhanced CT images sets: one CT images set (102) with hot point sources and a second CT image set (103) with point sources removed.

Still referring to FIG. 1, it is preferable to subtract (105) the two CT inputs (102 and 103) to remove background structures. For example, the E.SOFT® Image Registration activity, when in calibration mode, preferably subtracts the two CT inputs to remove background structures. The subtracted CT image and the NM image are inputted into a program (104) to isolate the point source images, calculate their positions, and to generate the FOV matrix (107), based essentially on Equations 6, described above. Equations 6 are illustrated as part of program (104) by box (106). Preferably, the calculated FOV-CM is stored in a local database (112) for future use. The local database can be in any form. Preferably, the local database is a DICOM database or a manufacturer-defined storage form.

As illustrated in FIG. 1, the NM reconstruction and image registration algorithms are preferably involved in automatically creating a field of view calibration matrix (FOV-CM) between CT and NM images. These algorithms are preferably only available in terms of E.SOFT® processing activities. The FOV-CM generated by the current SIEMENS SYMBIA® FOV calibration, is preferably saved into a local storage, and later retrieved and attached to the acquired NM projections.

According to various embodiments of the present invention, FOV-CM is preferably exported from E.SOFT® to a modular multimodal NM imaging system, and is later attached to the acquired NM data. According to other embodiments of the present invention, E.SOFT® saves FOV-CM into Generic Data Storage (GDS) and the reconstruction activities retrieve it from there.

Preferably, the E.SOFT® Image Registration activity also allows the user to align one of the input volumes to another, manually or automatically, to create a Transformation Matrix. The Transformation Matrix preferably represents a rigid orthogonal transformation between the two volumes, which is preferably stored in DICOM database along with the series UID [0020, 000E] and/or Frame Reference UID [0020, 0052] of the two. The series UID or Frame Reference UID preferably identifies the association of a Transformation Matrix to DICOM volumes. The Transformation Matrix preferably takes on the same mathematical form as described in Equation 1, i.e., a 4×4 matrix.

Figure 2:
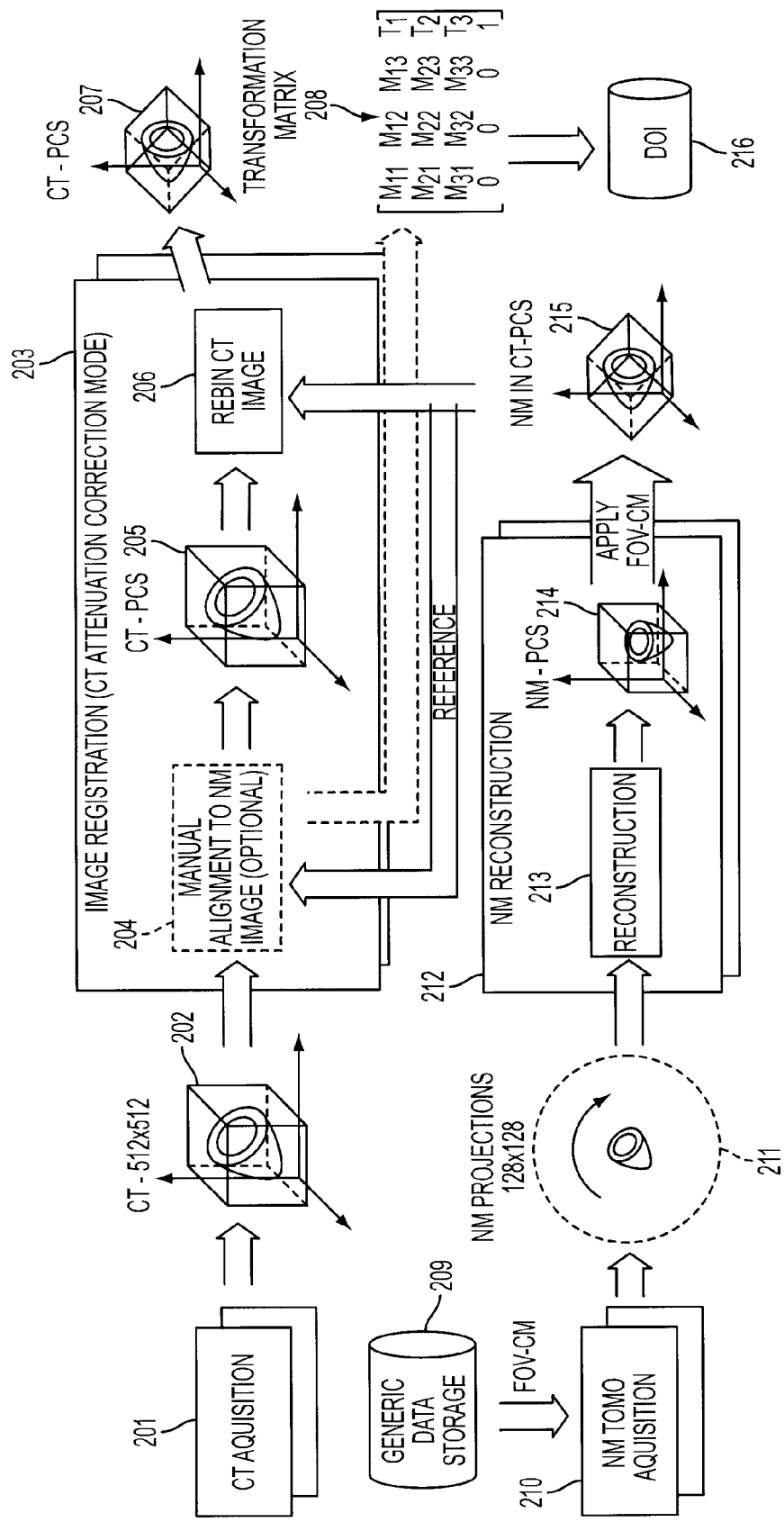
FIG. 2: shows a function block diagram representing how to adjust a computed tomography (CT) volume.

As shown in FIG. 2, the FOV-CM is preferably retrieved from the local storage (209). An NM projection image is preferably acquired during NM Tomo Acquisition (210). The FOV-CM is preferably attached to the acquired NM projection image in terms of a private DICOM attribute [0043, 1002]. The resultant NM projections (211) undergo an NM Reconstruction process (212). The NM Tomo reconstruction (213) is preferably performed and the reconstructed volume (214) is preferably transformed into CT-PCS space (215) by applying the FOV-CM that is preferably retrieved from the raw projection image in DICOM database.

The Image Registration Activity, in CT Attenuation Correction (AC) mode (203), re-bins (206) the CT volume (205) based on the location, orientation, and matrix and pixel sizes of the input NM image. The rebinned CT image (207) is preferably assigned the same Frame of Reference UID as that of the input NM image.

Due to patient motion between CT and NM scans, the user may need to manually align the CT image to the NM image via the display and manipulation tools on the UI page of the activity, as shown in FIG. 2, as dotted box (204). If the user manually adjusts the CT image while creating the rebinned CT volume, the raw CT (202) acquired in CT Acquisition (201) and FOV-CM corrected NM volume (215) are preferably re-registered. As shown by the dotted arrow in FIG. 2, a Transformation Matrix (208) is created and stored in DOI database (216), which is preferably used later for fusing and displaying CT and NM volumes by E.SOFT® or SYNGO® display tools. It is particularly preferable that the rebinned CT and the raw CT are registered via the same Transformation Matrix, because the rebinned CT shares the same Frame of Reference UID with the NM image.

Figure 3:
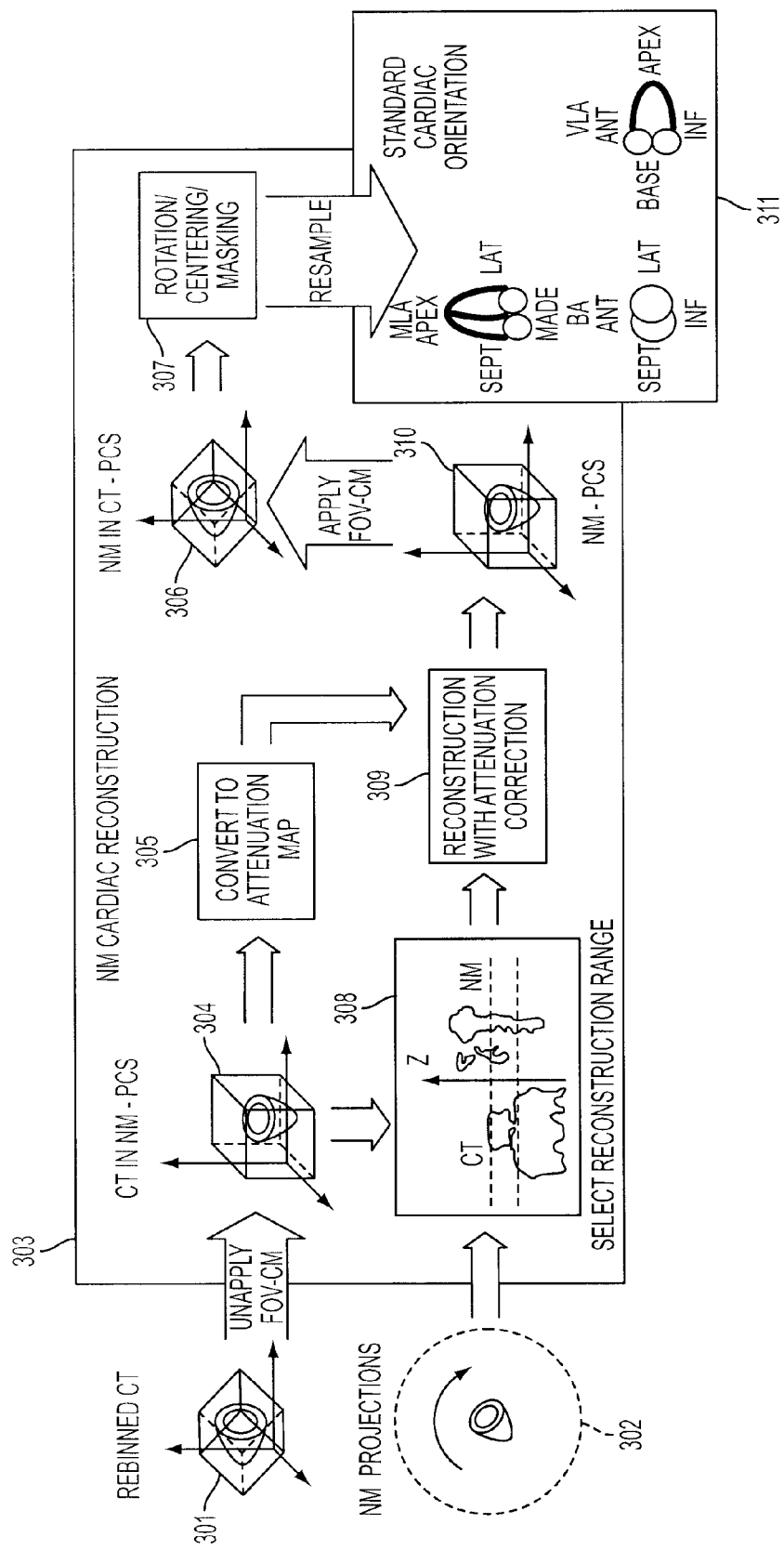
FIG. 3: shows a function block diagram representing how to perform a computed tomography (CT) attenuation correction (AC) reconstruction.

As shown in FIG. 3, NM reconstruction (303) is preferably performed with attenuation correction by using CT data. The E.SOFT® Autocardiac reconstruction activity is preferably designed to perform cardiac reconstructions with attenuation correction using the CT data.

Preferably, the rebinned CT data (301) is first adjusted to NM PCS, as illustrated at (304), using the FOV-CM. This adjustment is preferably made to match the raw NM coordinate system (302) based on a selected reconstruction range (308). Preferably, the attenuation map (305) is then calculated and the reconstruction of the user's choice is performed with each CT attenuation map slice properly applied to the reconstruction algorithm (309). Preferably, the FOV-CM is then applied to the NM in PCS (310) to form an NM reconstruction volume in CT-PCS (306). Preferably, the volume is finally rotated, shifted, and masked, as illustrated by box (307) to create an image of standard cardiac orientation (311).

Although the present invention has been described in considerable detail with reference to certain preferred versions thereof, other versions are possible. Therefore, the spirit and scope of the appended claims should not be limited to the description of the preferred versions contained herein.

The reader's attention is directed to all papers and documents which are filed concurrently with this specification and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in U.S.C §112, sixth paragraph. In particular, the use of "step of" in the claims herein is not intended to invoke the provisions of 35 U.S.C §112, sixth paragraph.

What is claimed is:

1. A method for correcting misalignment between a computed tomography (CT) image and a nuclear medical (NM) image in a modular multimodality imaging system, comprising:
identifying a difference between an NM patient coordinate system (PCS) with respect to a CT PCS by applying a field of view calibration matrix (FOV-CM) comprising a rotational transformation and a translational transformation of a spatial point that exists in both the NM PCS and in the CT PCS, and
aligning the CT image and the NM image based on the difference, and performing a cardiac reconstruction with attenuation correction by adjusting the CT PCS to match the NM PCS, calculating an attenuation map, performing a reconstruction based a CT attenuation map slice, applying the FOV-CM to form an NM reconstruction volume in CT-PCS, rotating, shifting, and masking the NM reconstruction volume in CT-PCS to create an image of standard cardiac orientation, wherein the steps above are performed using at least one processor.

2. The method according to claim 1, wherein the FOV-CM is generated by measuring the positions of three non-collinear points.

3. The method according to claim 1, wherein the FOV-CM is generated by subtracting two CT image sets to remove background structures and to isolate point images, and calculating positions of the point images.

4. The method according to claim 1, further comprising rebinning the CT image based on location, orientation, matrix size, and pixel size of the NM image.

5. A modular imaging system comprising:
a programmable element for correcting misalignment between a computed tomography (CT) image and a nuclear medical (NM) image in, the programmable element programmed to identify a difference of an NM patient coordinate system (PCS) with respect to a CT PCS by applying a field of view calibration matrix (FOV-CM) comprising a rotational transformation and a translational transformation of a spatial point that exists in both the NM PCS and in the CT PCS, and to align the CT image and the NM image based on the difference, wherein the programmable element is further programmed to perform a cardiac reconstruction with attenuation correction by adjusting the CT PCS to match the NM PCS, calculating an attenuation map, performing a reconstruction based a CT attenuation map slice, applying the FOV-CM to form an NM reconstruction volume in CT-PCS, rotating, shifting, and masking the NM reconstruction volume in CT-PCS to create an image of standard cardiac orientation.

6. The system according to claim 5, wherein the programmable element further programmed to generate the FOV-CM by measuring the positions of three non-collinear points.

7. The system according to claim 5, wherein the programmable element is further programmed to generate the FOV-CM by subtracting two CT image sets to remove background structures and to isolate point images, and calculating positions of the point images.

8. The system according to claim 5, wherein the programmable element is further programmed to rebin the CT image based on location, orientation, matrix size, and pixel size of the NM image.

* * * * *